US00PP29106P2

(12) United States Plant Patent
Berghman

(10) Patent No.: US PP29,106 P2
(45) Date of Patent: Mar. 13, 2018

(54) ***LEONTOPODIUM* PLANT NAMED 'BERGHMAN'**

(50) Latin Name: *Leontopodium alpinum*
Varietal Denomination: Berghman

(71) Applicant: Herman D. M. L. Berghman, Asse (BE)

(72) Inventor: Herman D. M. L. Berghman, Asse (BE)

( * ) Notice: Subject to any disclaimer, the term of this patent is extended or adjusted under 35 U.S.C. 154(b) by 0 days.

(21) Appl. No.: 15/330,391

(22) Filed: Sep. 14, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

PUBLICATIONS

UPOV hit on *Leontopodium* plant named 'Berghman', QZ PBR 20151485, filed Jun. 29, 2015.*

* cited by examiner

*Primary Examiner* — Anne M Grunberg
(74) *Attorney, Agent, or Firm* — Penny J. Aguirre

(57) ABSTRACT

A new cultivar of *Leontopodium*, 'Berghman', characterized by its long flower stems for good suitability as a cut flower, its large flowers, and its fast rate of propagation.

2 Drawing Sheets

Botanical classification: *Leontopodium alpinum.*
Variety denomination: 'Berghman'.

CROSS REFERENCE TO A RELATED APPLICATION

This application is related to a European plant breeders' rights application filed on Jun. 29, 2015, application No. 2015/1085. There have been no offers for sale anywhere in the world more than one prior to the filing of this Application and no accessibility to one of ordinary skill in the art could have been derived from the printed plant breeder's rights documents.

BACKGROUND OF THE INVENTION

The present invention relates to a new and distinct cultivar of *Leontopodium alpinum* and will be referred to hereafter by its cultivar name, 'Berghman'. 'Berghman' represents a new mountain flower for landscape use and for use as a cut flower in particular.

The new cultivar of *Leontopodium alpinum* was discovered in the Inventor's garden in spring of 2008 in Asse, Belgium as a chance seedling from 1,500 seeds he planted of unnamed and unpatented plants of *Leontopodium alpinum*. The Inventor selected 'Berghman' as a single unique plant amongst the seedlings in 2010.

Asexual propagation of the new cultivar was first accomplished by division by the Inventor in 2011 in Asse, Belgium. Asexual propagation by division, stem cuttings, and tissue culture intitiated from meristem tissue has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Berghman' as a unique cultivar of *Leontopodium.*

1. 'Berghman' exhibits very long flower stems for good suitability as a cut flower.
2. 'Berghman' exhibits large flowers.
3. 'Berghman' exhibits a fast rate of propagation.

The new *Leontopodium* can be most closely compared to the cultivars 'Matterhorn' (not patented) and 'Mt. Everest' (not patented). Both are similar to 'Berghman' in having flowers that are greenish white in color. Both 'Matterhorn' and 'Mt. Everest' differ from 'Berghman' in having smaller flowers, flowering stems that are half the length, and in being slower to propagate.

BRIEF DESCRIPTION OF THE DRAWINGS

The accompanying colored photographs illustrate the overall appearance and distinct characteristics of the new *Leontopodium*. The photographs were taken of plants about 3 years in age as field grown in Boskoop, The Netherlands and placed in a container for the photographs.

The photograph in FIG. 1 illustrates the plant habit of 'Berghman' in bloom.

Figure 1:
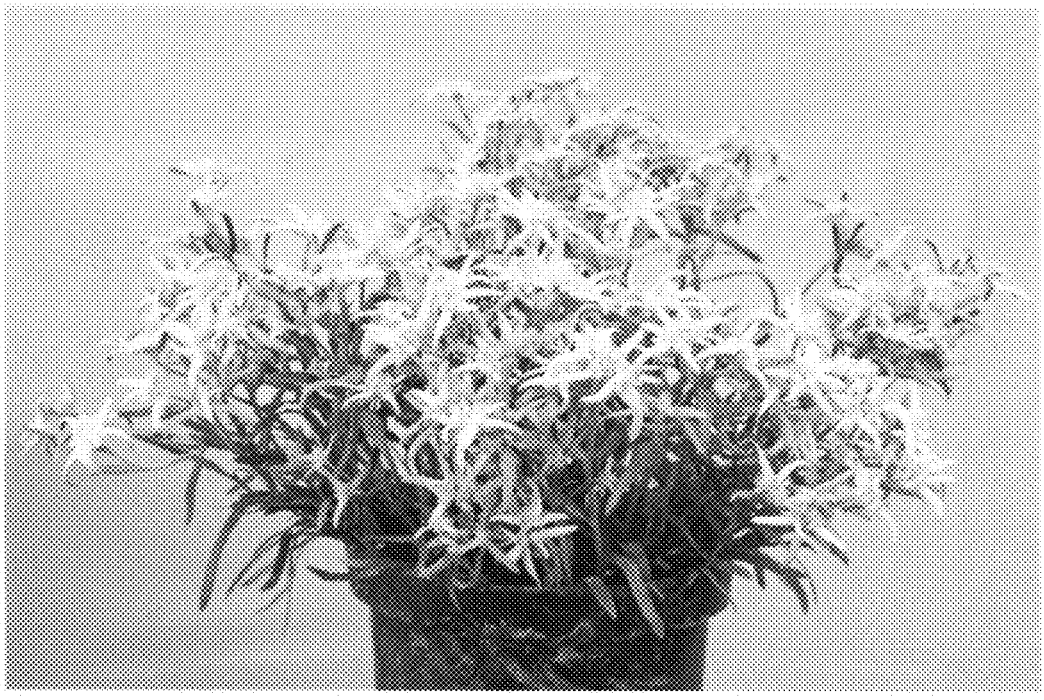
Figure 2:
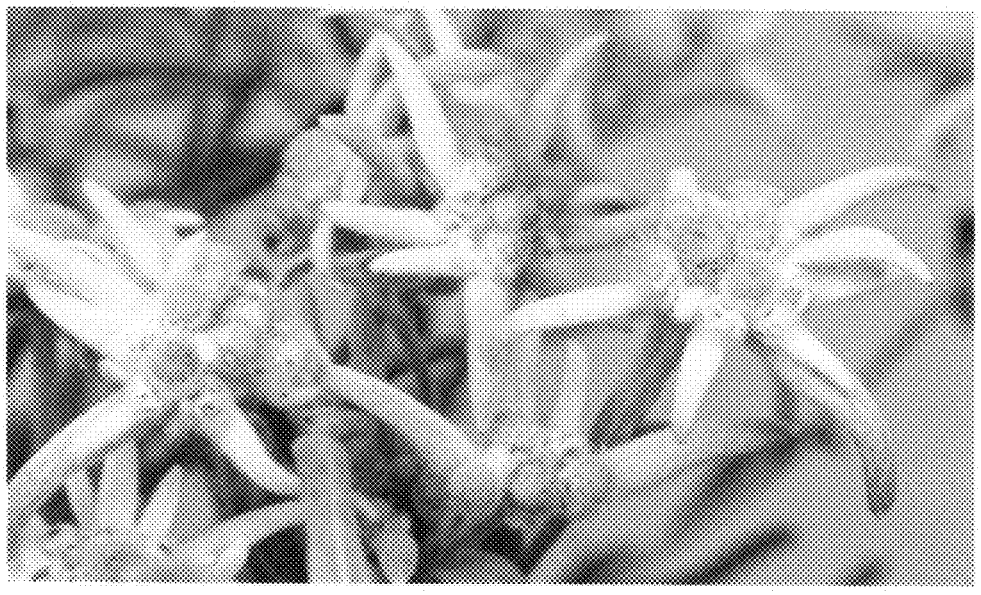

The photograph in FIG. 2 provides a close-up view of the flowers of 'Berghman'.

Figure 3:
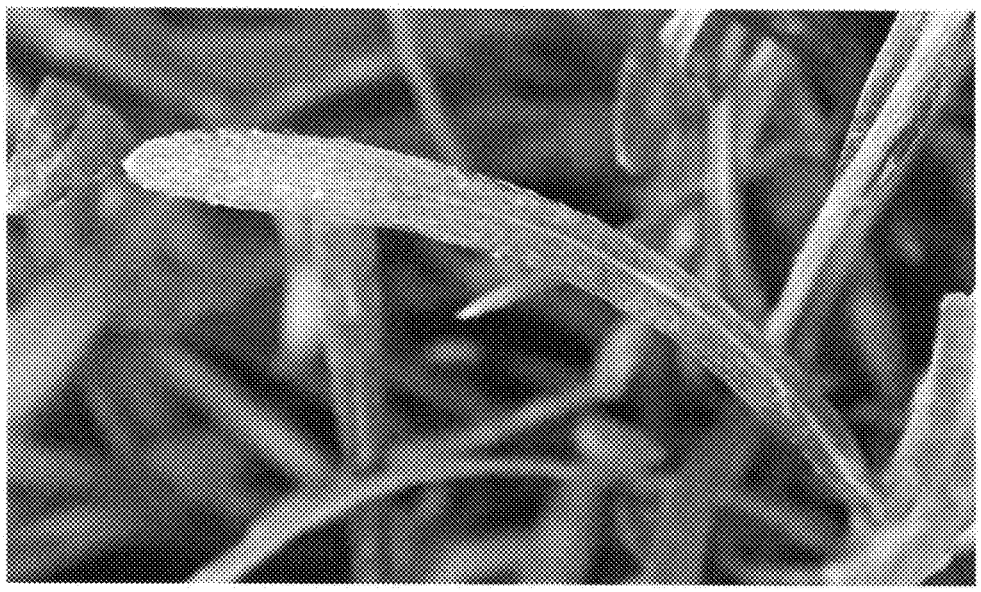

FIG. 3 provides a close-up view of a leaf of 'Berghman'.

The colors in the photographs may differ slightly from the color values cited in the detailed botanical description, which accurately describe the colors of the new *Leontopodium.*

BOTANICAL DESCRIPTION OF THE PLANT

The following is a detailed description of three year-old plants of the new cultivar as filed grown in Booskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General Description:

*Blooming period*.—Blooms continuously from mid-June to late August in Asse, Belgium.

*Plant type*.—Herbaceous perennial.

*Plant habit*.—Broad spreading, flattened globular.

*Height and spread*.—About 37 cm in height and 59.9 cm in width.

*Diseases*.—No susceptibility or resistance to diseases has been observed.

*Environmental tolerance*.—Rain tolerance; moderate, wind tolerance; high.

*Cold hardiness*.—At least to U.S.D.A. Zone 5.

*Root description*.—Fibrous roots.

*Growth rate*.—Vigorous for *Leontopodium*.

*Propagation*.—Division, stem cutting, and tissue culture using meristem tissue.

*Root development*.—A single division will produce about 8 new shoots in about 2 months.

Stem description: (Main flowering stems grow from the base, no lateral branches present).

*Stem shape*.—Rounded.

*Stem strength*.—Moderately strong.

*Stem color*.—146B.

*Stem surface*.—Densely covered with soft, thin adpressed hairs, an average of 2 mm in length and between NN155D and 157D in color.

*Stem size*.—Average of 29.9 cm in length and 3 mm in diameter.

*Stem aspect*.—Held at an average angle of 55° from the base, varying between 20° and 90°.

*Quantity*.—Average of 82 stems.

*Internode length*.—An average of 3.1 cm.

*Branching*.—Moderately branched.

Foliage description:

*Leaf division*.—Simple.

*Leaf shape*.—Lanceolate.

*Leaf base*.—Decurrent.

*Leaf apex*.—Acute.

*Leaf margin*.—Entire, revolute.

*Leaf venation*.—A main vein is present, upper surface is 145A in color, lower surface 148C in color, no lateral veins present.

*Leaf attachment*.—Sessile.

*Leaf arrangement*.—Alternate.

*Leaf number*.—An average of 10 leaves per stem 30 cm in length.

*Leaf surface*.—Upper surface; matte and soft to the touch, lower surface; slightly glossy, soft to the touch, both sides densely covered with soft, thin adpressed hairs, average of 2 mm in length and between NN155D and 157D.

*Leaf color*.—Young foliage; upper surface 138A, lower surface 138B to 138C, mature foliage; upper surface 137A, lower surface 138B.

*Leaf size*.—Average of 7.2 cm in length and 9 mm in width.

Inflorescence description:

*Type*.—Terminal raceme of capitulate, raceme.

*Capitulum number*.—Average of 26 inflorescences per lateral stem.

*Lastingness of inflorescence*.—About 3 weeks.

*Lastingness as a cut flower*.—About 7 days in water without additives.

*Capitulum*.—An average of 2.3 cm in height, 5.8 cm in diameter, held straight on top of main stems and lateral stems, consisting of disc florets only, disk size is an average of 9 mm in diameter, receptacle is an average of 1 mm in height and diameter and 144C in color and triangular in shape.

*Fragrance*.—Moderately strong, sweet and slightly musky.

*Involucral bracts*.—Average of 30, arranged in 2 rows, average 4 mm in length and 1 mm in width, ovate in shape, acute apex, cuneate base, entire margin, upper surface texture; glabrous, lower surface texture; matte, very densely covered with soft pubescence an average of 2 mm in length and between NN155D and 157D, color; upper surface; 146A to 146B, lower surface; 146B to 146C, covered with very dense pubescence, an average length of 2 mm in length and between NN155D and 157D.

*Buds*.—Globular in shape, an average of 4 mm in length and diameter, 143C in color, the bud is covered with very dense and soft pubescence and average of 2 mm in length and between NN155D and 157D in color.

*Peduncle*.—Terminal peduncle; 5 mm in length, 1.5 mm in diameter, strong, held straight upright, fourth peduncle; 6.3 cm in length, 1.5 mm in diameter, strong, and held at an angle of 55°, both peduncles are densely covered with soft adpressed hairs and average of 2 mm in length and between NN155D and 157D in color, color is between 144A and 146B, strong.

*Ray florets*.—No ray florets present.

*Disk florets* (*bisexual*).—Numerous, average of 120, spirally placed on disc, narrow tubular, acute apex, upper 10% free, base fused into tube, average of 4.5 mm in length, 0.5 mm in width, both surfaces glabrous and glossy, when opening and fully open, mature and immature; 145C to 145D.

Reproductive organs (present on disk florets only):

*Gynoecium*.—Pistil; 1, average of 7.5 mm in length, style; 7 mm in length and 145D in color, ovary is 145D in color.

*Androcoecium*.—Stamens; not all disc florets hold stamen, an average of 1 disc floret hold stamen, there is an average of 5 stamens per disc floret, filament; average of 3.5 mm in length and 145D in color, anther; linear in shape, 2 mm in length and 1C in color, pollen; low in quantity and 5D in color.

*Fruit/seed*.—None observed.

It is claimed:

1. A new and distinct cultivar of *Leontopodium* plant named 'Berghman' substantially as herein illustrated and described.

* * * * *